(12) United States Patent
Coulon et al.

(10) Patent No.: US 12,115,040 B2
(45) Date of Patent: Oct. 15, 2024

(54) NOISE REDUCTION AND IDENTIFICATION DEVICE FOR ACOUSTIC PROTECTION HEADSET

(71) Applicant: APPI-TECHNOLOGY SAS, Nimes (FR)

(72) Inventors: Denis Coulon, Nîmes (FR); Hippolyte Nioche, Nimes (FR)

( * ) Notice: Subject to any disclaimer, the term of this patent is extended or adjusted under 35 U.S.C. 154(b) by 210 days.

(21) Appl. No.: 17/936,395

(22) Filed: Sep. 29, 2022

(65) Prior Publication Data

US 2023/0107802 A1     Apr. 6, 2023

(30) Foreign Application Priority Data

Oct. 1, 2021   (FR) ....................................... 2110407

(51) Int. Cl.
*A61F 11/14*     (2006.01)
*H04R 1/08*     (2006.01)
*H04R 1/10*     (2006.01)

(52) U.S. Cl.
CPC .............. *A61F 11/145* (2022.01); *H04R 1/08* (2013.01); *H04R 1/1008* (2013.01); *H04R 1/1041* (2013.01); *H04R 1/1083* (2013.01); *H04R 2430/01* (2013.01)

(58) Field of Classification Search
CPC ....... A61F 11/145; H04R 1/08; H04R 1/1008; H04R 1/1041; H04R 1/1083; H04R 2430/01
USPC .................................. 381/72, 312, 317, 71.1
See application file for complete search history.

(56) References Cited

U.S. PATENT DOCUMENTS

| | | | |
|---|---|---|---|
| 2008/0263749 A1 | 10/2008 | Leong et al. | |
| 2009/0205900 A1 | 8/2009 | Purcell et al. | |
| 2016/0193084 A1* | 7/2016 | Jenkins ............ | G10K 11/17853 381/72 |
| 2022/0386018 A1* | 12/2022 | Everman .......... | G10K 11/17821 |

FOREIGN PATENT DOCUMENTS

| | | |
|---|---|---|
| WO | 2009/139682 A1 | 11/2009 |
| WO | 2009/139682 A8 | 11/2009 |

* cited by examiner

*Primary Examiner* — Thjuan K Addy
(74) *Attorney, Agent, or Firm* — Patshegen IP; Moshe Pinchas

(57) ABSTRACT

The noise reduction and identification device adapts itself to a predetermined acoustic protection headset comprising two shells interconnected by means of mechanical links mounted on each shell removably at the end of two cylindrical shafts with collinear axes.
The device comprises an envelope made of elastic material of internal shape matching part of the external shape of at least one of the shells, said envelope having:
  openings corresponding to the shafts and
  around these openings, a thickness less than the distance between the mechanical connection mounted on a shell and said shell.
The elastic material constituting the casing has a coefficient of elasticity such that the deformation of the casing necessary for the opening corresponding to a shaft to deviate sufficiently from the shell for this shaft to come out entirely from this opening, is reversible.

11 Claims, 13 Drawing Sheets

NOISE REDUCTION AND IDENTIFICATION DEVICE FOR ACOUSTIC PROTECTION HEADSET

TECHNICAL FIELD OF THE INVENTION

The present invention relates to a noise reduction and identification means for acoustic protection headphones.

STATE OF THE ART

Noise-canceling headsets/headphones are used to preserve hearing from sounds that are too loud and potentially dangerous for the ear and, by extension, for the health of its user. From 80 dB(A), we speak of a harmful noise level. In case of daily exposure of 80 dB(A), the employer must provide hearing protection equipment. From 85 dB(A), employees are obliged to wear hearing protection. In addition to the risk of deafness, prolonged exposure to noise can have multiple effects on the body, for example the risk of accidents, cardiovascular disorders or stress.

When sound intensities exceed 85 dB(A) or 137 dB(C), the wearing of personal hearing protectors ("PHP") is mandatory. The maximum tolerated sound power not to be exceeded is 87 d(B) or 140 dB(C) taking into account the attenuation of PHPs. The first passive noise canceling headsets were made of fibrous or porous materials such as mineral wool or glass wool with acoustic properties. However, these devices are not able to provide adequate protection against low frequencies sounds. Professional noise canceling headsets are specially designed to reduce the intensity of perceived noise in the workplace. Indeed, the professional noise canceling headphones are able to reduce noise between 20 dB and 37 dB.

PRESENTATION OF THE INVENTION

The present invention aims to remedy all or part of these drawbacks.

To this end, the present invention relates, according to a first aspect, to a noise reduction and identification means for a predetermined acoustic protective headset comprising two shells connected to each other by means of mechanical connections mounted, on each shell of removable manner at the end of two cylindrical shafts with collinear axes, device which comprises an envelope made of elastic material of internal shape matching part of the external shape of at least one of the shells, said envelope having:
  openings corresponding to the shaft and
  around these openings, a thickness less than the distance between the connection mounted on a shell and said shell;
  the elastic material constituting the casing having a coefficient of elasticity such that the deformation of the casing necessary for the opening needed for the to deviate sufficiently from the shell for this shaft to come out entirely from this opening, is reversible.

Thanks to these provisions, the envelope is removable without irreversible deformation, which makes it possible to form intervention teams whose envelopes are of the same color, by changing these envelopes. And, since this envelope is removable, the user can choose to wear the headset without these envelopes, for example to reduce the total weight of the headset. The device that is the subject of the invention also provides the following advantages to the headset on which it is mounted on:

better resistance to splashing water,
better resistance to dust: the shells are perfectly protected against dust and
better mechanical resistance to shocks and falls, due to the elasticity of the envelopes.

In embodiments, the material constituting the envelope and said thickness are jointly configured so that the envelope attenuates by at least two decibels, and preferably by at least four decibels, the average sound intensity for pink noise in the band from 125 Hz to 8 KHz, inside the shell.

Thus, the device that is the subject of the invention makes it possible to better protect the hearing of wearers of acoustic protection since additional acoustic attenuation is obtained.

In some embodiments, the casing comprises at least one depressing zone designed with a touching identifiable relief, intended to be positioned over a button of a shell of the acoustic protection headset when the envelope partially covers said shell.

Thanks to these arrangements, the headset operating control buttons remain accessible and recognizable through the flexible envelope.

In embodiments, the envelope includes an opening for passing a microphone boom. Thanks to these provisions, the device that is the subject of the invention is compatible with headsets equipped with a microphone.

In embodiments, the envelope is made of a material comprising rubber and/or silicone.

The inventors have found that rubber and silicone are favorable materials both for compliance with the coefficient of elasticity and the need for acoustic attenuation.

In embodiments, the envelope is made of a material comprising silicone.

The inventors have found that silicone is also a favorable material both for compliance with the coefficient of elasticity and the need for acoustic attenuation.

In some embodiments, the device that is the subject of the invention is manufactured by molding the material constituting the casing and drilling the openings.

Thanks to these provisions, the manufacture of the casing is simplified and the manufacturing tolerances are reduced.

According to a second aspect, the present invention relates to a set of two devices which are objects of the invention, the envelopes of which are of the same color, one of which comprises at least one manual depressing zone designed with a touching identifiable relief, intended to be positioned over a button of a shell of the acoustic protection headset when the envelope partially covers said shell and the other does not include such a support zone.

One of the envelopes is thus adapted to one of the shells of the headset, while the other is adapted to the other shell of the headset. In addition, the envelopes being of the same color, they make it possible to identify a team of which the wearer of the headset is a member.

In some embodiments, the device comprising at least one depressing zone comprises an opening for the passage of a microphone boom and the device not comprising such a depressing zone does not comprise an opening for the passage of a microphone boom.

According to a third aspect, the present invention aims at a set of a plurality of sets of devices which are objects of the invention having a plurality of different colors.

According to a fourth aspect, the present invention relates to a kit comprising at least one device which is the subject of the invention and at least one clip configured to retain the lips of a slot formed in an envelope up to one of its edges.

According to a fifth aspect, the present invention relates to a kit comprising at least one acoustic protection headset comprising two shells connected to each other by means of mechanical connections mounted on each shell in a removable manner at the end of two cylindrical shafts with collinear axes, and at least two devices according to the invention configured to envelop, at least partially, the shells of at least one said headset.

The advantages, aims and characteristics of this kit, this set and these kits being similar to those of the device that is the subject of the invention, they are not repeated here.

BRIEF DESCRIPTION OF FIGURES

Other advantages, aims and particular characteristics of the invention will emerge from the non-limiting description which follows of at least one particular embodiment of the noise reduction and identification device for the acoustic protection headset which is the subject of the present invention, facing the attached drawings, in which.

DESCRIPTION OF EMBODIMENTS

Figure 1:
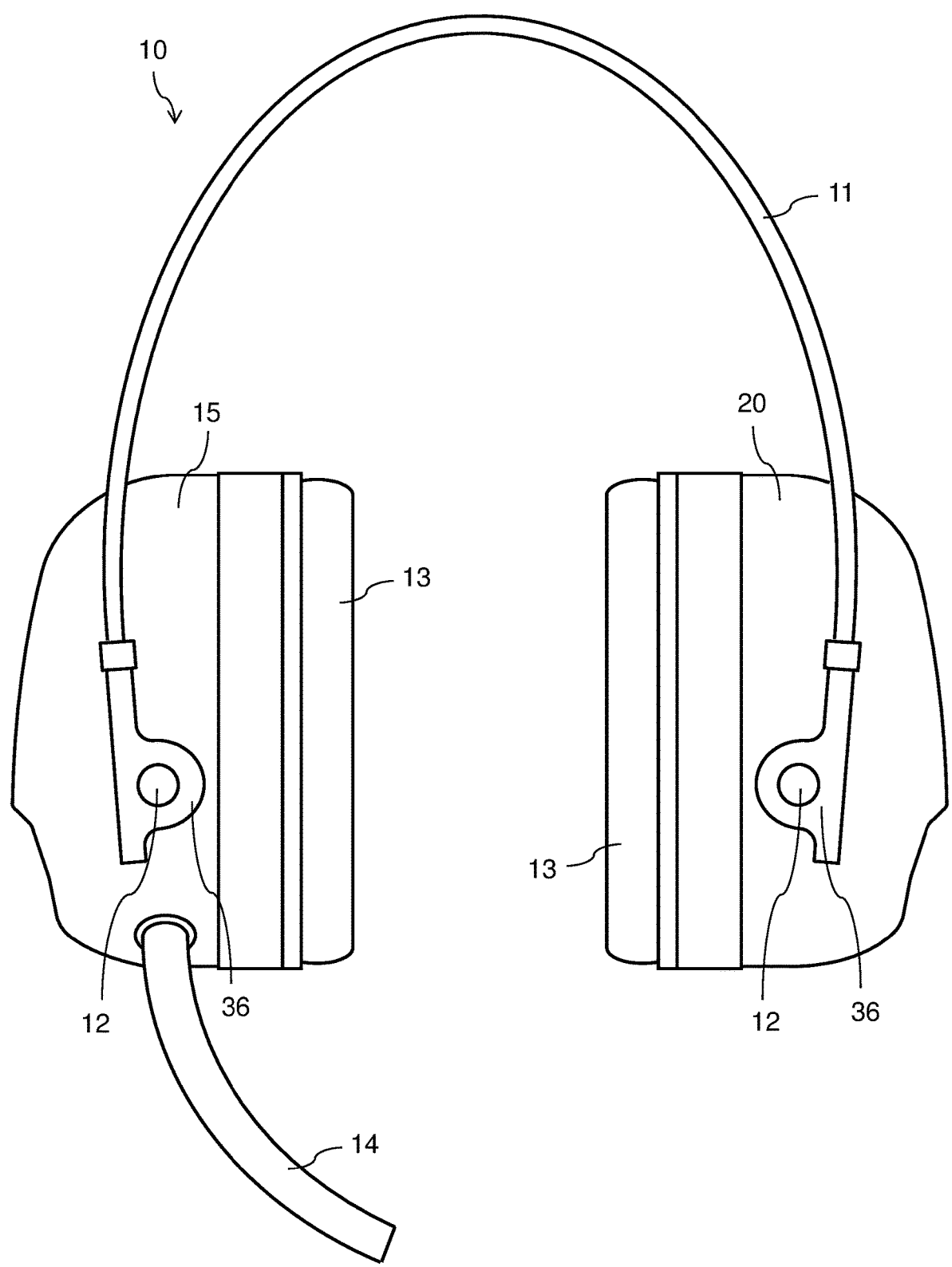
FIG. 1 shows, in front view, a noise-canceling headset without a device that is the subject of the invention.

This description is given on a non-limiting basis, each characteristic of an embodiment being able to be combined with any other characteristic of any other embodiment in an advantageous manner.

We note, from now on, that the FIGS. are each to scale and that the scales of the different FIGS. can be different.

Throughout the description, "upper" or "top" means what is at the top or oriented upwards, in FIGS. 1 to 8, FIGS. which correspond to the configuration of normal use of the device and of the noise-canceling headphones. We call "lower" or "low", what is below or directed downwards, in these FIGS. The notions of vertical and horizontal, as well as heights, derive from these definitions. What is called "front view" is what is visible when looking at the face of the user wearing the noise-canceling headphones, possibly equipped with the device that is the subject of the invention. What is called "sideways" is what is visible when looking at the profile of the face of the user wearing the noise-canceling headphones, possibly equipped with the device that is the subject of the invention.

We call "internal" what is close to or oriented towards the head of the user and "external", what is far away or oriented away from this head.

FIGS. 1 to 4 show an acoustic protection headset 10, to which is adapted at least one device 25 which is the subject of the invention illustrated in FIGS. 5 to 8. The headset 10 is thus predetermined for the realization, by the person skilled in the art, of each device 25 object of the invention adapted to cooperate with this headset 10.

The headset 10 comprises two shells 15 and 20 interconnected via mechanical connections 36. In the embodiment represented in FIGS. 1 to 12, these mechanical connections 36 are at the end of a hoop 11. In other embodiments (not shown), these mechanical connections 36 are supported by a protection helmet. The present invention is, of course, adaptable to any type of headset comprising two shells, whatever the type of mechanical connections connecting the two shells.

Shell 15 is intended to cover the user's right ear and shell 20 to cover the user's left ear. Each shell 15 and 20 has a support pad 13 on the user's head. Shell 15 carries a microphone boom 14.

Figure 3:
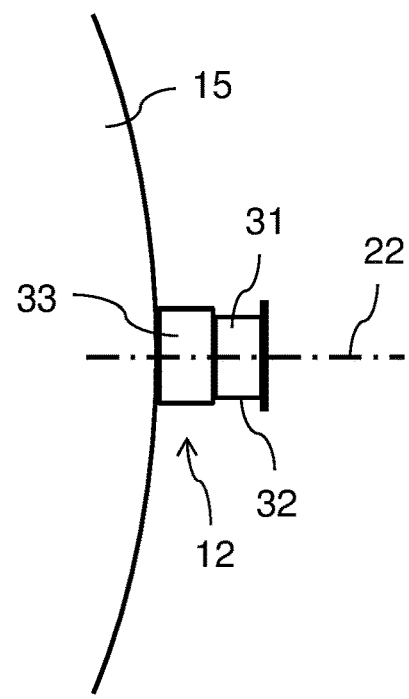
FIG. 3 shows, in partial side view, a branch clip for fixing a noise-canceling headset without a device that is the subject of the invention.
Figure 4:
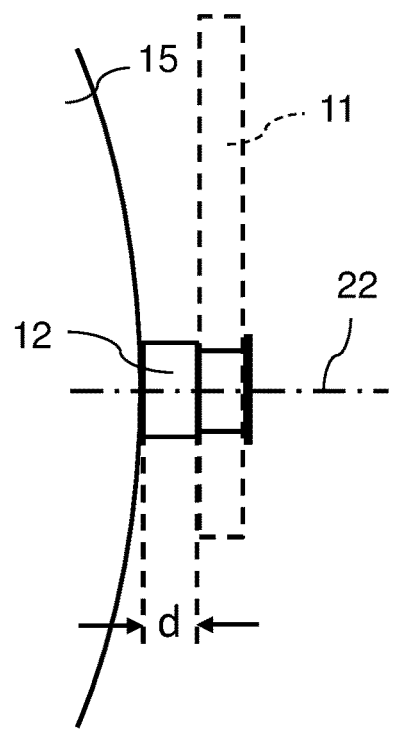
FIG. 4 shows, in partial side view, a noise-canceling headset with attachment of the temple and without a device that is the subject of the invention.
Figure 5:
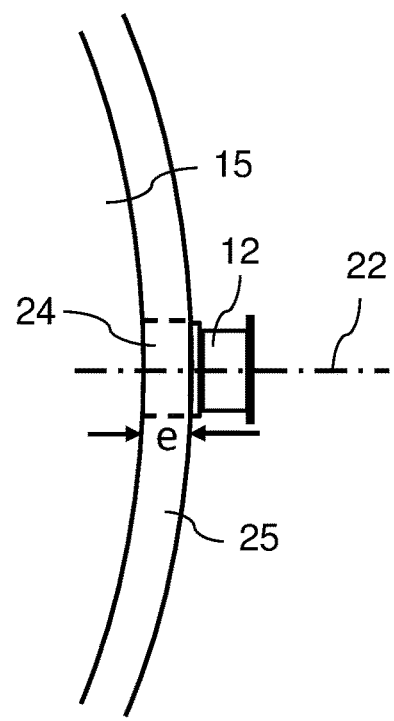
FIG. 5 shows, in partial side view, a fastening arm attachment of a noise-canceling headset fitted with the device that is the subject of the invention.
Figure 6:
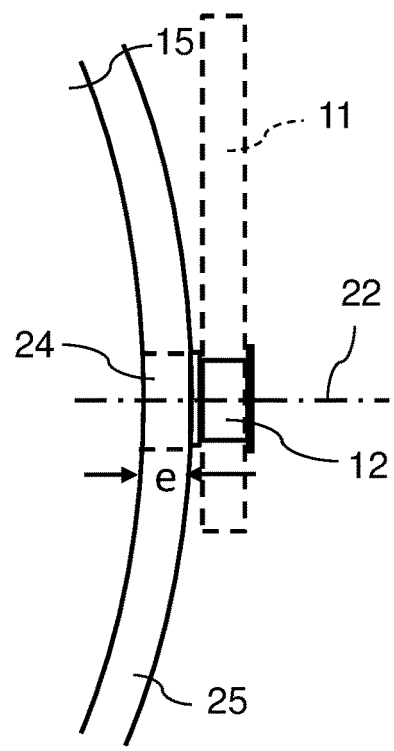
FIG. 6 shows, in partial side view, a noise-canceling headset with attachment arm attachment fitted with the device that is the subject of the invention.
Figure 7:
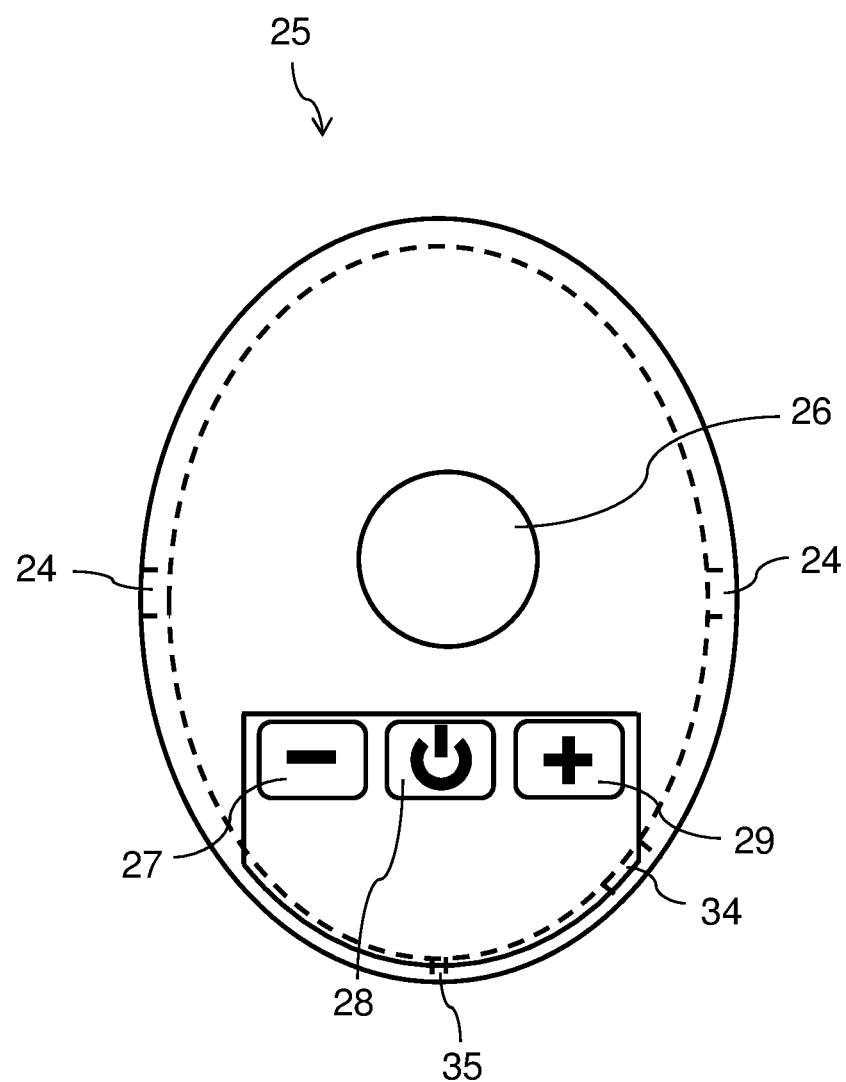
FIG. 7 shows, in side view, a device that is the subject of the invention.
Figure 8:
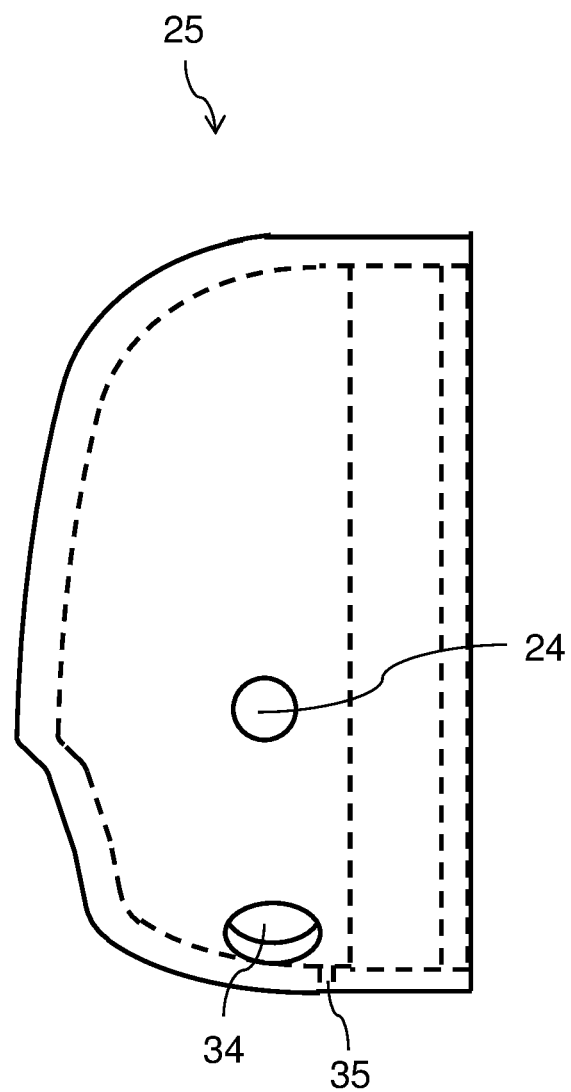
FIG. 8 shows, in front view, a device that is the subject of the invention.

The mechanical connections 36 of the hoop 11 or of the hard hat are mounted, on each shell 15 and 20, in a removable manner at the end of two cylindrical shafts 12 with collinear axes 22. As illustrated in FIGS. 3 and 4, each shaft 12 preferably comprises:

- a first part 33, proximal because attached to the shell 15 or 20, preferably cylindrical with a circular director, of a first diameter and
- a second part 31, distal, having a cylindrical groove 32 with a circular director, of a second diameter less than the first diameter, intended to receive a connection 36 carried by the arch 11 or a construction headset, in a pivot connection of axis 12, as illustrated in FIG. 4.

This attachment 12, from connection 36 to shell 15 or 20, leaves a distance "d" (see FIG. 4) free between connection 36 and shell 15 or 20.

Of course, other types of attachment of the connection 36 to the shell 15 or 20 make it possible to leave free a distance between this connection 36 and the shell 15 or 20.

The present invention is compatible with all these types of attachment.

Figure 2:
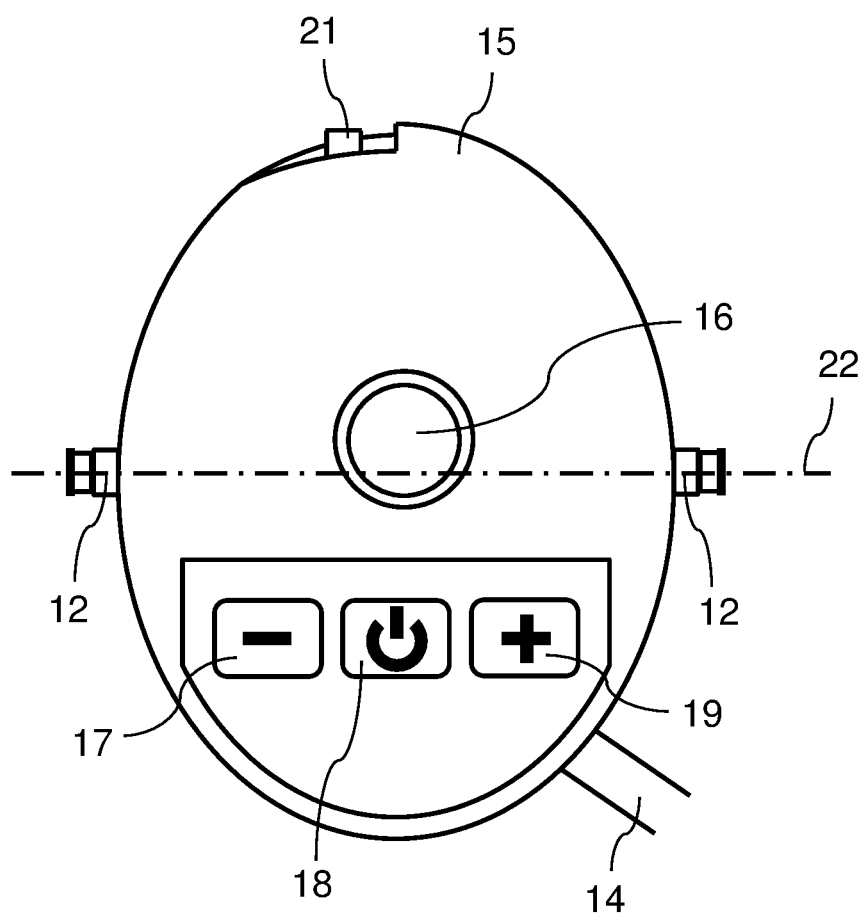
FIG. 2 shows, in side view, a noise-canceling headset shell fitted with a microphone, without attachment arm and without device that is the subject of the invention.

As illustrated in FIG. 2, the shell 15 has buttons for controlling the operation of the audio part of the headset 10:

a button 16 which controls the Push-To-Talk mode (also called "Push-To-Talk)" or "PTT", which is a conversation method on a half-duplex link (for example via a transceiver), relying on the press of a button to switch from reception mode to transmission mode, a button 17 which controls a reduction in the sound intensity emitted by the speaker (not shown) present in the shell 15, a button 18 which controls a stop or the power supply of the electrical or electronic components of the headset 10, a button 19 which controls an increase in the sound intensity emitted by the loudspeaker (not shown) present in the shell 15.

Buttons 17, 18 and 19 bear, on the side, finger identification reliefs. The button 17 carries, in relief, a form of "–". The button 18 bears, in relief, a logo for switching on or off. The button 19 carries, in relief, a form of "+".

Furthermore, a connector 21 makes it possible to connect an external radio frequency antenna.

As illustrated in FIGS. 5 to 10, the casing 25 of the device is preferably one-piece, that is to say formed from a single block, for example by molding. At the level of the shafts 12, the casing 25 comprises through openings 24. The casing 25 has, around the shafts 12, a thickness "e" (see FIG. 6) less than or equal to the distance "d". We note that the thickness of the envelope is modulated, in particular to increase the elasticity around the crossing elements (fasteners, cable, etc.) and to match the shapes of these elements or, on the contrary, to increase sound attenuation at a distance of these elements.

The casing 25 is preferably a one-piece casing, that is to say made up of a single piece. The casing 25 also has an opening 34 for the passage of the microphone boom 14 and a through opening 35 for the evacuation of water that can pass between the casing 25 and the shell 15.

The envelope 25 also has manual support zones provided with finger identification reliefs, 26, 27, 28 and 29 corresponding respectively to the buttons 16, 17, 18 and 19 and having the same reliefs as these, respectively. Thus, the control buttons 16, 17, 18 and 19 for operating the headset 10 remain accessible and recognizable through the flexible envelope 25.

Figure 9:
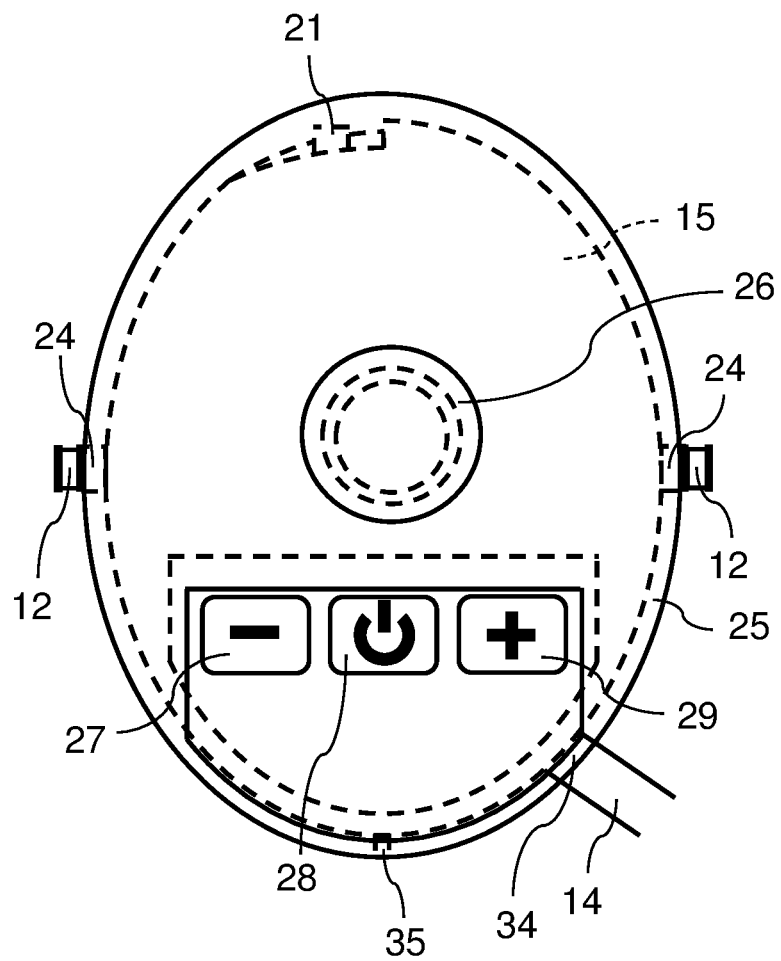
FIG. 9 shows, in side view, a device that is the subject of the invention mounted on a shell of a noise-cancelling headset equipped with a microphone.
Figure 10:
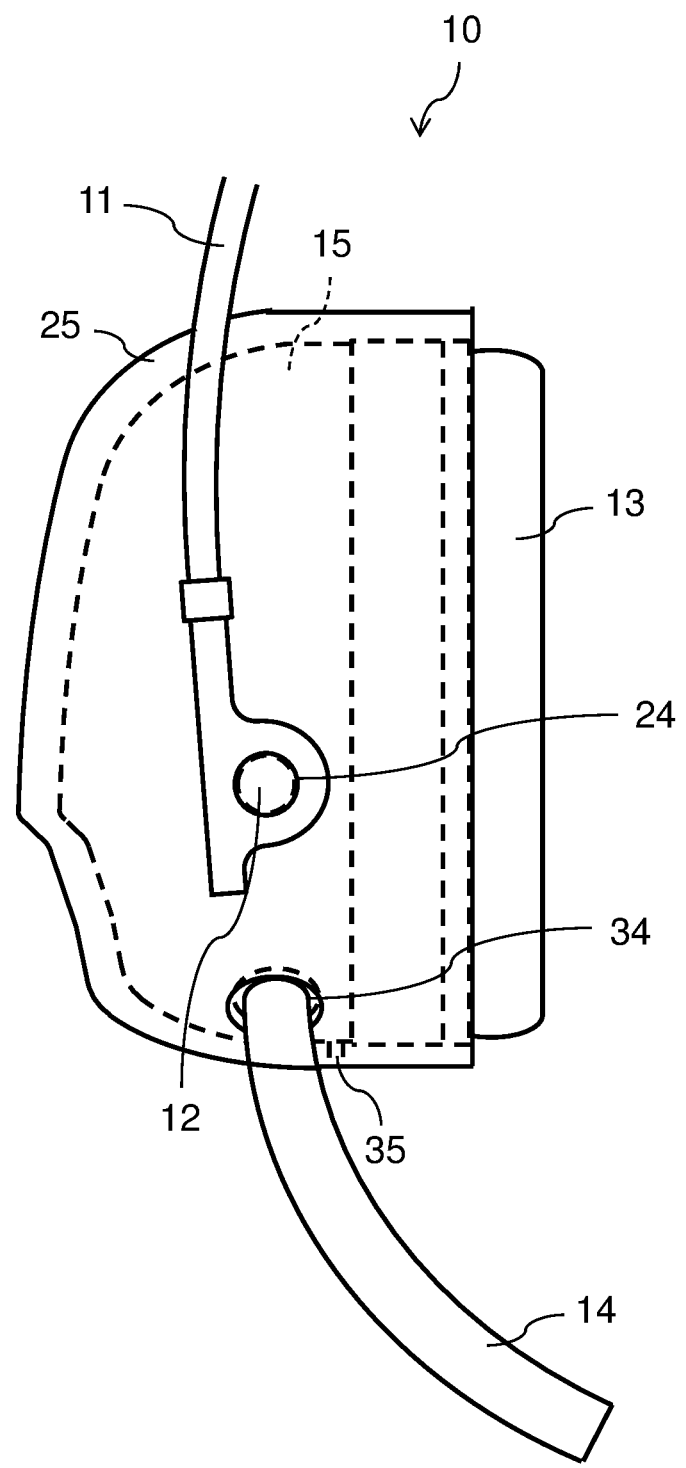
FIG. 10 shows, in front view, a device that is the subject of the invention mounted on this noise-canceling headset shell fitted with a microphone.

As illustrated in FIGS. 9 and 10, in which the shell 15 is shown in broken lines, once fitted to the shell 15, the casing 25 conforms to a part, preferably all, except the pad 13, of the external shape of the shell 15.

Figure 11:
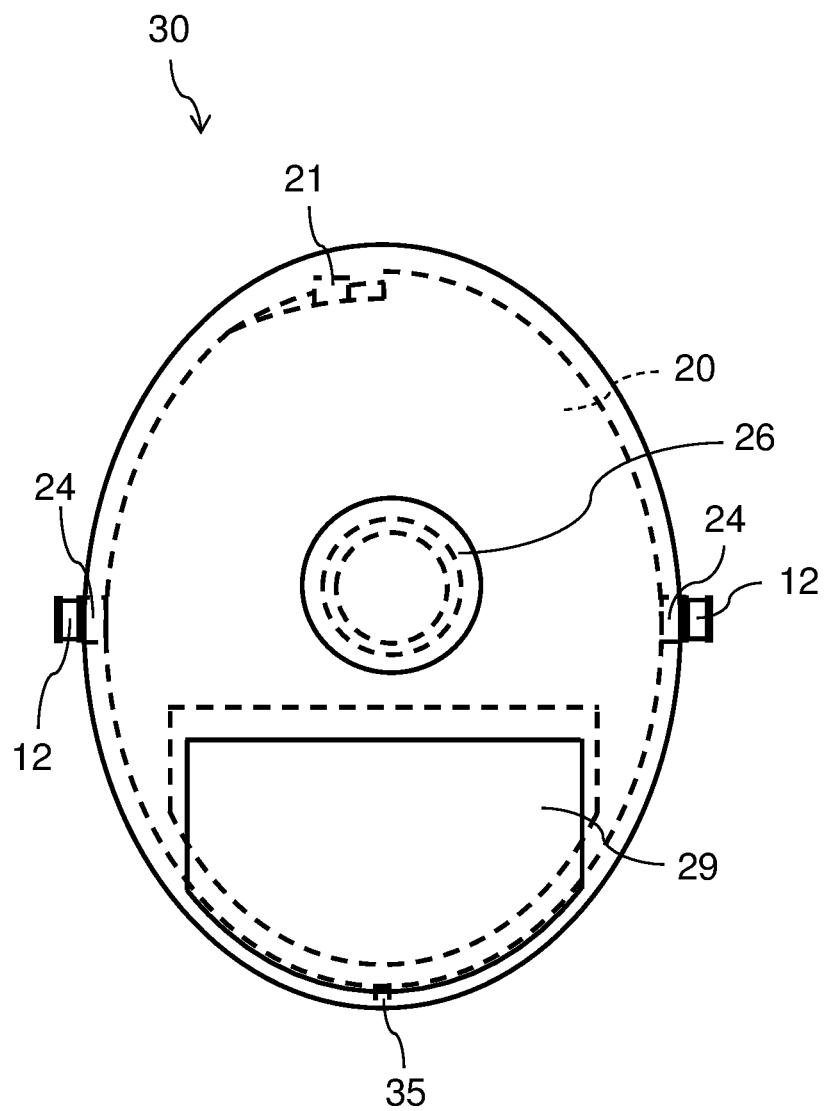
FIG. 11 shows, in side view, a device that is the subject of the invention mounted on another shell of a noise-cancelling headset fitted with a microphone.
Figure 12:
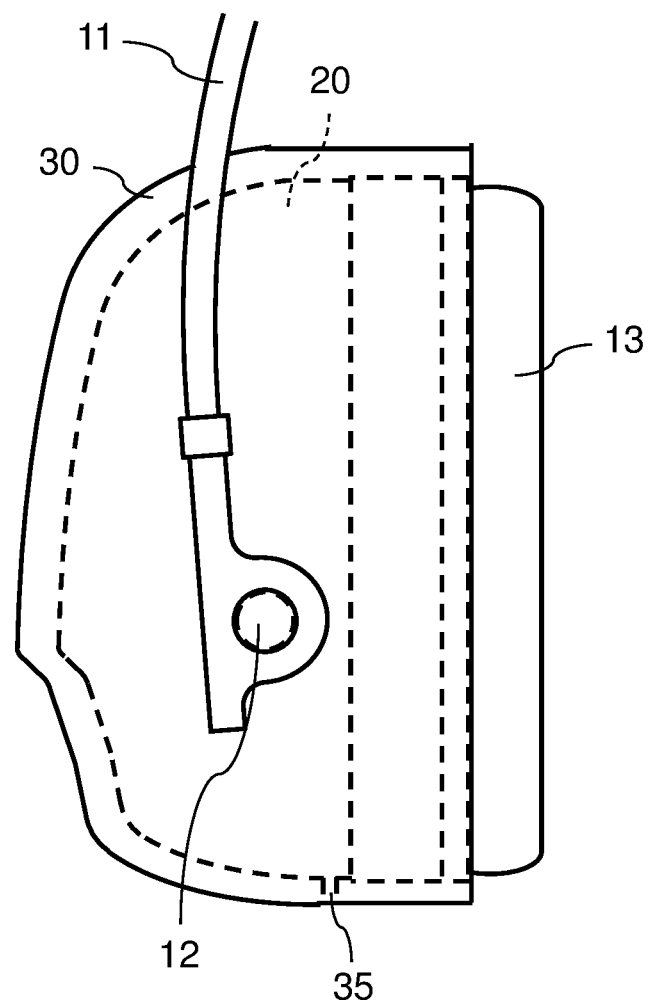
FIG. 12 shows, in front view, a device that is the subject of the invention mounted on this other noise-canceling headset shell fitted with a microphone.

As illustrated in FIGS. 11 and 12, an envelope 30 intended to cover the shell 20 has neither an opening 24 for a microphone boom nor button shapes.

A set of envelopes 25 and 30 makes it possible to cover the two shells 15 and 20 of the same headset 10. Preferably, these two envelopes 25 and 30 have the same color, in order to facilitate the visual identification of the members of the same team, for example an intervention team whose all members are linked by radio communications.

Preferably, a set of a plurality of sets of devices that are objects of the invention has a plurality of different colors in order to be able to constitute and visually identify the members of different teams.

The headsets 10 and the casings 25 and 30 can also be associated in kits which are the subject of the invention comprising at least one acoustic protection headset 10 comprising two shells 15 and 20 connected to each other by means of mechanical connections 36 mounted on each shell 15 and 20 removably at the end of two cylindrical shafts 12 with collinear axes and at least one set of two devices 25 and 30 objects of the invention configured to envelop, at least partially, the shells 15 and 20 by at least minus such a headset 10.

The material constituting the envelope 25 and the thickness of the envelope 25 are preferably jointly configured so that the envelope attenuates by at least two decibels, and preferably by at least four decibels, the average sound intensity for a noise rose in the band of 125 Hz to 8 KHz, inside shell 15.

Note that the measured attenuation is not the same according to the frequency bands but also according to the reference intensities and the type of noise (white, pink, etc.). The inventors have observed attenuations of up to seven decibels with pink noise at an average of 70 dB, in the frequency band from 125 Hz to 8 KHz, by implementing the materials and thicknesses mentioned above.

The elastic material constituting the casing 25 has a coefficient of elasticity such that the deformation of the casing 25 necessary for the opening 24 corresponding to a shaft 12 to deviate sufficiently from the shell 15 for this shaft 12 to come out completely of this opening 24, is reversible.

A person skilled in the art knows how to choose the material and the thickness of the casing 25 to obtain these results.

Preferably, the material constituting the envelope 25 and the thickness of the envelope 25 are jointly configured so that the envelope 25 attenuates by at least four decibels the average sound intensity for pink noise in the 125 Hz interval. at 8 KHz, inside the shell 15.

For example, a casing 25 made of rubber, for example of the Shore 40A tinted silicone type, with an average thickness preferably between 2.5 and 4 mm, makes it possible to achieve this result.

As can be understood on reading the preceding description, the envelopes 25 and 30 are removable without irreversible deformation, which makes it possible to form intervention teams whose members are in radio communication and whose envelopes are of the same color, by changing these envelopes 25 and 30 of the headsets 10. In addition, the device 25 or 30 which is the subject of the invention makes it possible to better protect the hearing aid of the wearers of acoustic protection headsets since an additional acoustic attenuation is obtained by their positioning on the shells of the headset 10. And, since these envelopes 25 and 30 are removable, the user can choose to wear the headset 10 without these envelopes, for example to reduce the total weight of the headset.

In embodiments, the envelopes 25 and 30 are manufactured by molding the material constituting the envelope and drilling the openings 24 and 34. The manufacture of the envelopes 25 and 30 is thus simplified and the manufacturing tolerances are reduced, which allows to guarantee sound attenuation and the mechanical strength of the envelopes.

An example of a kit comprising a headset 10 and shells 25 and 30 forms a noise-canceling headset that includes a radio, which makes it possible to have a full-duplex communication system with very long range, without additional audio accessories. Envelopes 25 and 30 increase the attenuation by 3, 4, or even 5 dB. An average over the range (125 Hz-8 KHz) of 4 dB is very important because the protective headset 10 provides attenuation greater than 30 dB, or even 33 dB, a guarantee of very good protection in extreme environments (aeronautics, transport, heavy industry). It is noted that the material constituting the envelopes is transparent for the wavelengths of the radio communications used.

In some embodiments, the elements (boom microphone, electric cable between the two shells, etc.) are not removable on the headset shells. In the embodiment shown in the FIGS., the microphone boom is passed through a hole in the casing 25 to install it.

Regarding the cable between the shells, fixed, of an already mounted headset to which envelopes are to be adapted, a slot 72 is provided in the envelope reaching the edge of each envelope and allowing the cable to be inserted into an opening 73 at the end slot 72. Once the cable has passed through this slot 72, this slot 72 is closed to keep the adhesion effect of the envelope which tends to shrink since it is elastic.

In some embodiments, each envelope is associated with a clip 60 (see FIGS. 14 to 17), for example made of rigid plastic material, in a housing provided in the thickness of the envelope. This clip 60 maintains edge to edge the lips of the slot 72, by means of studs 63, 64, 65, 66 passing through notches made in the casing.

Thus, it is possible to remove, change and replace the casings on the shells by inserting the clips 60 under the area of the casing surrounding the slot 72. The lips of the slot are thus contiguous, which limits acoustic insulation leaks.

The device, removable envelopes which is the subject of the invention, thus becomes compatible with any pre-existing headset. Envelopes are designed for a particular headset, creating a slot 72, if necessary, and placing a staple 60 in it after the cable is passed through the slot 72.

In the example of clip 60 illustrated in FIGS. 14 to 17, clip 60 comprises a plate 61 whose inner face 62 intended to rest on shell 15 or 20 is concave with a concavity in correspondence with the convexity of the shell 15 or 20 instead of where clip 60 will be placed.

On the face of the plate 61 opposite the concave face 62, are positioned two mushroom-shaped studs, each formed of a cylindrical body, 64 and 66 respectively, and of a head, 63 and 65 respectively, overhanging all the generators of the corresponding cylindrical body. The height of each cylindrical body 64 and 66 is greater than or equal to the thickness of the edge of the envelope 25 or 30 intended to be stapled, as illustrated in FIG. 16.

The studs are symmetrical to each other with respect to a plane of symmetry (not shown, vertical and comprising the slot 72, in FIGS. 16 and 17) of the clip 60. Prisms 67 and 68, which are also symmetrical relative to this plane, have increasing thicknesses towards this plane of symmetry. The envelope 25 or 30 has concave housings 75 (see FIG. 17) whose internal volume is equal to the external volume of these prisms 67 and 68. These housings 75 of prisms 67 and 68 can form part of a larger housing whose interior volume corresponds to the exterior volume of the clip 60 and receives it entirely, such that the exterior surface of the casing is little or not deformed by the presence of the clip 60 under its edge.

Rounded edges 69 of prisms 67 and 68 are arranged on the side of these premiums closest to studs 63 to 66.

Figure 16:
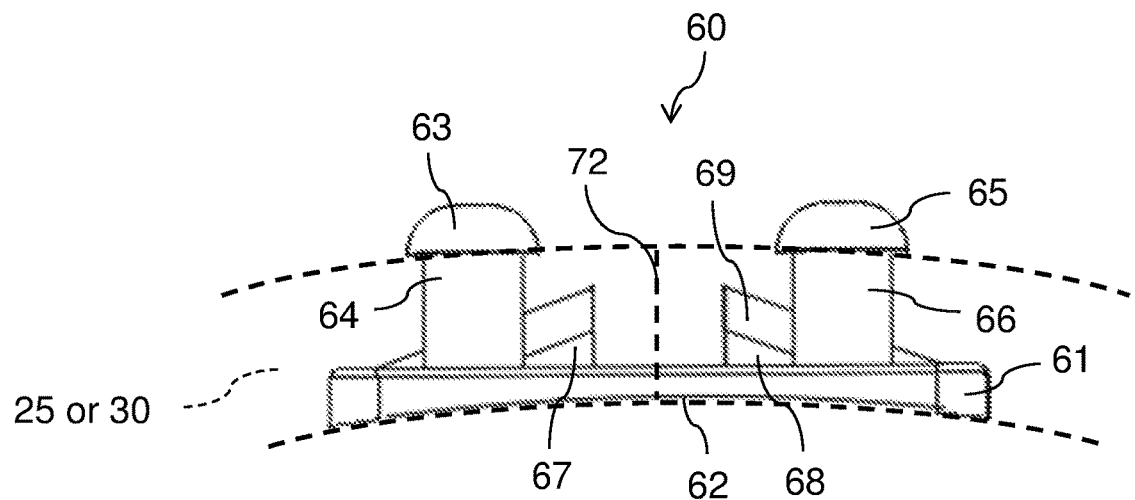
FIG. 16 shows, in side view, the clip illustrated in FIGS. 14 and 15 and, in broken lines, an envelope of the device that is the subject of the invention.
Figure 17:
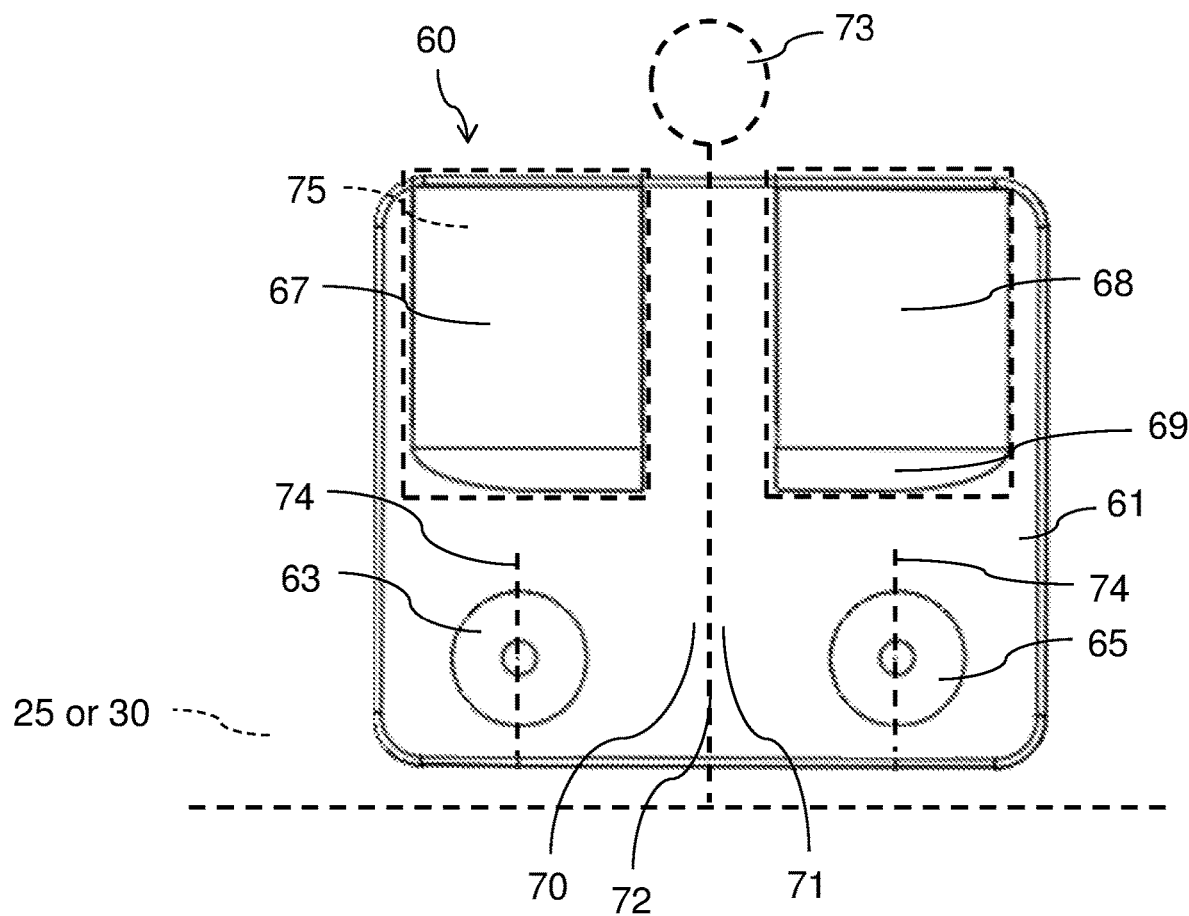
FIG. 17 shows, in top view, the clip illustrated in FIGS. 14 to 16 and, in broken lines, an envelope of the device that is the subject of the invention.

As illustrated in FIGS. 16 and 17, a slot 72 formed in the envelope 25 or 30 and reaching its edge separates two lips 70 and 71. At the end of the slot 72, a circular opening 73 is intended for the passage of a headset cable, for example the cable connecting the two shells 15 and 20 to convey the electrical and/or audio signals.

Once this cable has been positioned in this opening 73, a clip 60 is inserted under the lips 70 and 71 until the prisms 67 and 68 are housed in the housings 75. Then the studs 63 to 66 are passed through slots 74 formed in the envelope 25 or 30 and does not open onto the edge of this envelope. The studs retain the lips 70 and 71, which are then contiguous, which prevents sound insulation leaks.

The present invention also relates to a kit comprising at least one device according to the invention and at least one clip configured to retain the lips of a slot formed in an envelope and extending as far as one of its edges.

Figure 13:
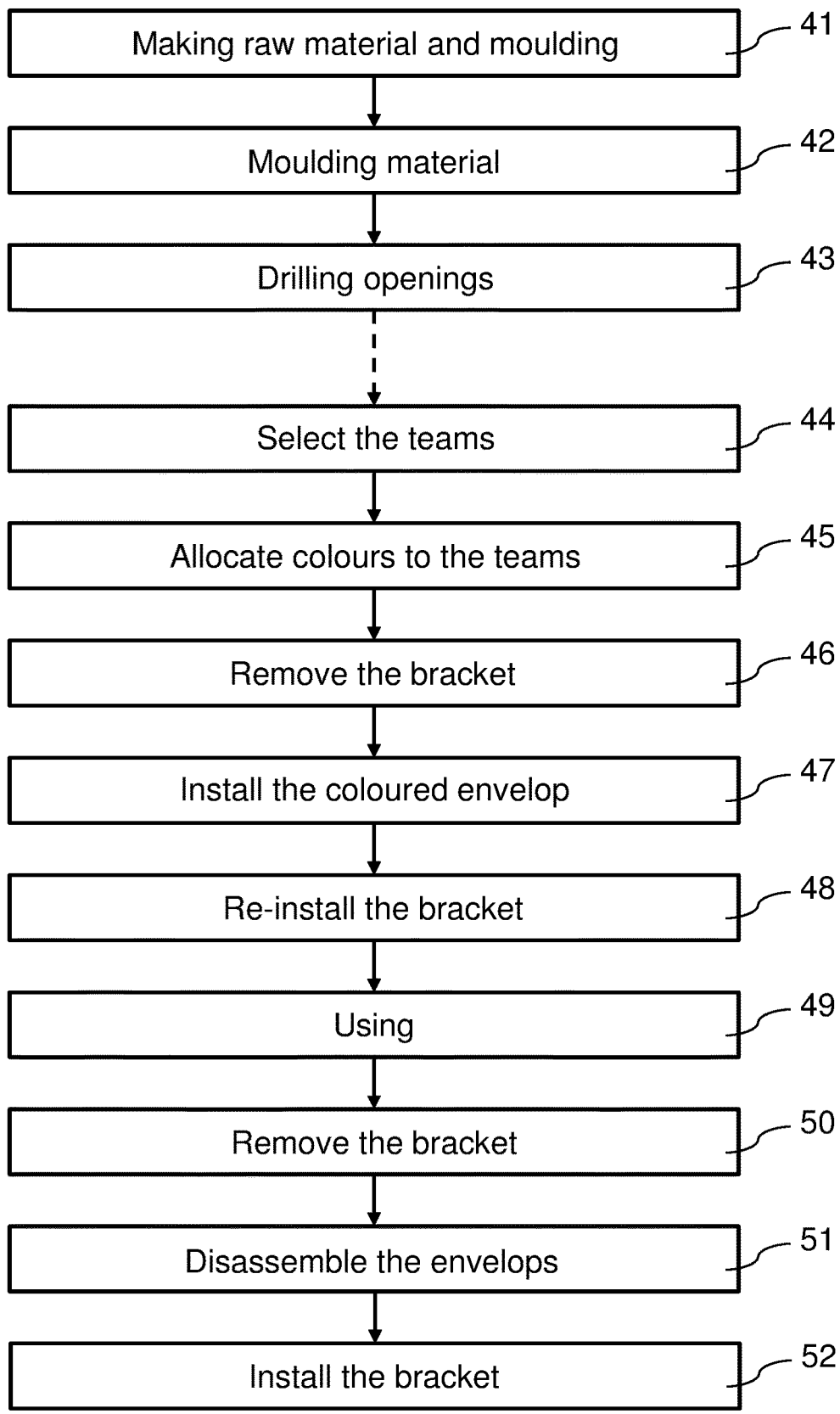
FIG. 13 represents, in the form of a flowchart, a manufacture and use of the device that is the subject of the invention.
Figure 14:
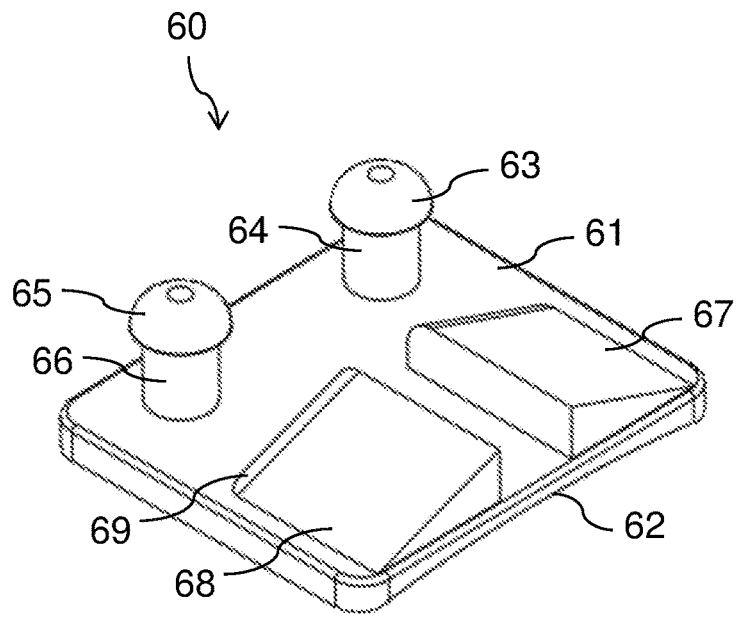
FIG. 14 represents, according to a first perspective, an embodiment of a clip for closing a slot of an envelope of the device object of the invention.
Figure 15:
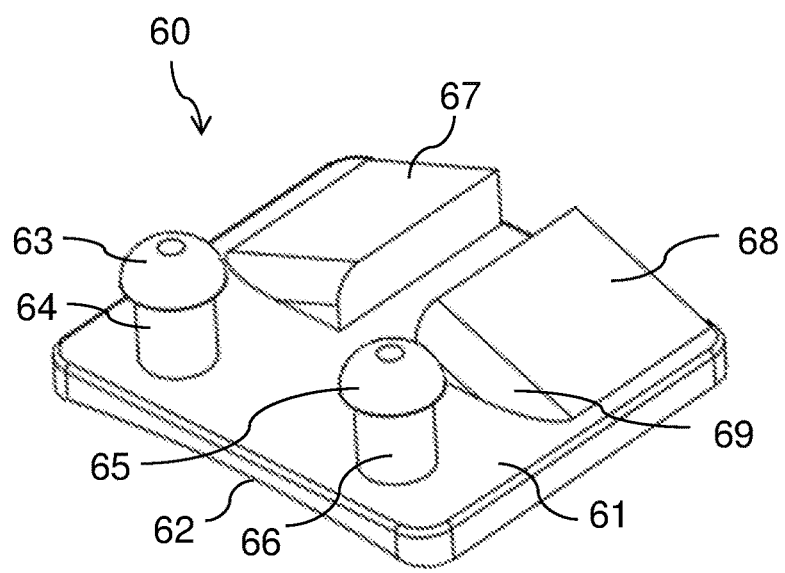
FIG. 15 shows, from a second perspective, the staple illustrated in FIG. 14.

We observe, in FIG. 13, steps of manufacture and use of the device object of the invention. During a step 41, the material and the molds suitable for a predetermined protective headset are formed. During a step 42, the envelopes are molded. During a step 43, the through openings are drilled, in particular 24, for the two envelopes, and 34 for the envelope intended for the shell carrying a microphone boom. The envelopes are then distributed in the form of sets, without the headset or associated with a headset to constitute a kit.

Regarding the use of the devices, during a step 44, headsets are assigned to members of different teams. During a step 45, each team is assigned a particular color of envelopes. During a step 46, for each headset, the fasteners 12 of the shells are separated, on the one hand, and the connections 36, on the other hand. During a step 47, an envelope of the color corresponding to the team that is going to use the headset is placed on each shell of each headset. For an envelope to be placed on a shell, a first shaft 12 is placed in a first opening 24. Then, the edge of the envelope is deformed, in a reversible manner, at the level of the other shaft 12 until than this edge then surrounds the shaft 12 and position the shaft 12 in an opening 24.

During a step 48, said connections 36 are reassembled. During a step 49, the headset is used, in a manner known per se. During a step 50, for each headset, said connections 36 are separated from the fasteners 12 of the shells. During a step 51, the envelopes are removed, according to the procedure opposite to that of laying, with reversible deformation of the edges of the envelopes. During a step 52, said links 36 are reassembled on the attachments 12 of the shells.

The invention claimed is:

1. A noise reduction and identification device for a predetermined acoustic protection headset comprising two shells interconnected by means of mechanical connections mounted on each shell removably at the end of two cylindrical shafts with colinear axes, device that comprises an envelope of elastic material of internal shape matching part of the external shape of at least one of the shells, said envelope having:
    openings corresponding to the shafts and
    around these openings, a thickness e less than the distance d between the mechanical connection mounted on a shell and said shell;
    wherein the elastic material constituting the casing has a coefficient of elasticity such that the deformation of the casing necessary for the opening corresponding to a shaft to deviate sufficiently from the shell for this shaft to come out entirely from this opening, is reversible.

2. The device of claim 1, wherein the material constituting the envelope and said thickness are jointly configured so that the envelope attenuates by at least two decibels, and preferably by at least minus four decibels, the average sound intensity for pink noise in the 125 Hz to 8 KHz range, inside the shell.

3. The device of claim 1, wherein the casing comprises at least one manual support zone provided with a relief of finger identification, intended to be positioned opposite a button of a shell of the headset for acoustic protection when the envelope partially covers said shell.

4. The device of claim 1, wherein the casing has an opening for the passage of a microphone boom.

5. The device of claim 1, wherein the envelope is made of a material comprising rubber and/or silicone.

6. The device of claim 1, which is manufactured by molding the material constituting the casing and drilling the openings.

7. A set of two devices of claim 1 of the same color, a first of said devices comprising at least one depressing zone provided with a finger touch-identifiable relief, intended to be positioned over a button of a shell of a headset for acoustic protection when the envelope partially covers said shell and a second of said devices not comprising such a bearing zone.

8. The set of two devices of claim 7, wherein the first device comprising an opening for the passage of a pole for a microphone and the second device not comprising an opening for the passage of a microphone boom.

9. A group of a plurality of sets of two devices of claim 7 having a plurality of different colors.

10. A kit comprising at least one device of claim 1 and at least one clip configured to retain lips of a slot formed in an envelope up to one of its edges.

11. A kit comprising at least one headset for acoustic protection comprising two shells interconnected by means of mechanical connections mounted on each shell in a removable manner at the end of two shafts cylindrical having collinear axes and at least two devices of claim 1 configured to cover, at least partially, the shells of at least one said headset.

* * * * *